US008475774B2

(12) United States Patent
Clemente et al.

(10) Patent No.: US 8,475,774 B2
(45) Date of Patent: Jul. 2, 2013

(54) SUNSCREEN COMPOSITIONS COMPRISING AN ULTRAVIOLET RADIATION-ABSORBING POLYMER

(75) Inventors: Rudy Clemente, Montreal (CA); Curtis Cole, Ringoes, NJ (US); Susan Daly, Basking Ridge, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 260 days.

(21) Appl. No.: 13/020,915

(22) Filed: Feb. 4, 2011

(65) Prior Publication Data

US 2011/0195036 A1    Aug. 11, 2011

Related U.S. Application Data

(60) Provisional application No. 61/302,219, filed on Feb. 8, 2010.

(51) Int. Cl.
*A61K 8/00* (2006.01)
*A61K 8/18* (2006.01)
*A61K 8/49* (2006.01)

(52) U.S. Cl.
USPC .............. 424/59; 424/60; 424/70.9; 514/937; 514/938; 516/53; 516/72; 516/75

(58) Field of Classification Search
None
See application file for complete search history.

(56) References Cited

U.S. PATENT DOCUMENTS

| | | | |
|---|---|---|---|
| 4,107,290 | A | 8/1978 | Jacquet et al. |
| 4,489,057 | A | 12/1984 | Welters et al. |
| 4,524,061 | A | 6/1985 | Cho et al. |
| 4,528,311 | A | 7/1985 | Beard et al. |
| 4,611,061 | A | 9/1986 | Beard et al. |
| 4,919,934 | A | 4/1990 | Deckner et al. |
| 5,063,048 | A | 11/1991 | Saitoh et al. |
| 5,243,021 | A | 9/1993 | Langer et al. |
| 5,372,804 | A | 12/1994 | Khoshdel et al. |
| 5,403,944 | A | 4/1995 | Frater et al. |
| 5,487,885 | A | 1/1996 | Sovak et al. |
| 5,565,531 | A | 10/1996 | Blank |
| 5,714,134 | A | 2/1998 | Richard et al. |
| 5,741,924 | A | 4/1998 | Sovak et al. |
| 5,776,439 | A | 7/1998 | Raspanti et al. |
| 5,783,173 | A | 7/1998 | Bonda et al. |
| 5,869,030 | A | 2/1999 | Dümler et al. |
| 5,993,789 | A | 11/1999 | Bonda et al. |
| 6,018,044 | A | 1/2000 | Huber |
| 6,123,928 | A | 9/2000 | Sovak et al. |
| 6,193,959 | B1 | 2/2001 | Bernasconi et al. |
| 6,338,838 | B1 | 1/2002 | Berset et al. |
| 6,376,679 | B2 | 4/2002 | Leduc et al. |
| 6,800,274 | B2 | 10/2004 | Bonda et al. |
| 6,899,866 | B2 | 5/2005 | Bonda |
| 6,962,692 | B2 | 11/2005 | Bonda et al. |
| 2004/0028626 | A1 | 2/2004 | Candau |
| 2005/0186154 | A1 | 8/2005 | Bonda et al. |
| 2006/0286053 | A1 | 12/2006 | Dueva-Koganov et al. |
| 2007/0092457 | A1 | 4/2007 | LiBrizzi et al. |
| 2007/0092458 | A1 | 4/2007 | LiBrizzi et al. |
| 2007/0098653 | A1 | 5/2007 | Tamasawa et al. |
| 2008/0280997 | A1 | 11/2008 | Rodier et al. |
| 2009/0098367 | A1 | 4/2009 | Wenzel et al. |
| 2009/0324523 | A1 | 12/2009 | Cole et al. |
| 2009/0324524 | A1 | 12/2009 | Cole et al. |
| 2009/0326182 | A1 | 12/2009 | Cole et al. |
| 2010/0196291 | A1 | 8/2010 | Halimi et al. |

FOREIGN PATENT DOCUMENTS

| | | |
|---|---|---|
| EP | 0 273 202 A | 7/1988 |
| EP | 0 897 716 A | 2/1999 |
| EP | 0 897 716 B | 2/1999 |
| EP | 1166761 A | 1/2002 |
| FR | 2818143 A | 6/2002 |
| FR | 2892633 A | 5/2007 |
| JP | 9239311 A | 9/1997 |
| JP | 10316726 A | 12/1998 |
| JP | 11001420 A | 1/1999 |
| JP | 2004-292555 A | 10/2004 |
| WO | WO 90/03809 A | 4/1990 |
| WO | WO 93/04665 A | 3/1993 |
| WO | WO 01/08647 A | 2/2001 |
| WO | WO 2008/081175 A | 7/2008 |
| WO | WO 2009/038710 A | 3/2009 |

OTHER PUBLICATIONS

Vavilikolanu et al. "The Development and Utilization of an In Vitro Safety Testing Program for Hair Conditioners", presented at the 47th Annual Society of Toxicology Meeting in Seattle, WA; Mar. 17-20, 2008.*
U.S. Patent Documents—None.*
NPL search results from SciFinder search performed by the Examiner on Mar. 27, 2013.*
Vavilikolanu et al., "Experiences in the development and utilization of an in vitro safety testing program for hair conditioners", *AATEX, Proc. 6th World Congress on Alternatives & Animal Use in the Life Sciences*, Mar. 31, 2008, vol. 14, Special Issue, pp. 529-534.
Aultz, "The Development of a Polymerisable Benzotriazole Stabiliser", Speciality Chemicals (1996) vol. 16, No. 2, pp. 71-74.
Bonda et al., Cosmetic & Toiletries Magazine (2002) vol. 115, No. 6, pp. 37-45.
Janssen Pharmaceutica, Material Safety Data Sheet, NORBLOC® 6000 (Apr. 1997).
Janssen Pharmaceutica, Material Safety Data Sheet, NORBLOC® 7966 (Apr. 1997).
Steward et al, "Catalytic Chain Transfer Polymerisation of Functional Methacrylates", internet article [Online] 1998, pp. 1-11. URL: <http://www.warwick.ac.uk/fac/sci/Chemistry/polymers/downloads/stewardascm1998.pdf> [retreived on Oct. 29, 2009].
McCain et al, "Cell Biology and In Vitro Toxiciology", The Toxicologist 66(1-S), 243 (1981).

* cited by examiner

*Primary Examiner* — Robert A Wax
*Assistant Examiner* — Jeffrey T Palenik

(57) ABSTRACT

Aqueous compositions including a discontinuous oil phase containing an ultraviolet radiation-absorbing polymer stabilized in a continuous aqueous phase, an oil-gelling polymer, and which are substantially free of non-polymeric ultraviolet radiation-absorbers.

17 Claims, No Drawings

SUNSCREEN COMPOSITIONS COMPRISING AN ULTRAVIOLET RADIATION-ABSORBING POLYMER

This application claims the benefit of U.S. provisional application 61/302,219 filed Feb. 8, 2010, the complete disclosure of which is hereby incorporated herein by reference for all purposes.

FIELD OF THE INVENTION

The present invention relates to topically-acceptable sunscreen compositions comprising UV-absorbing polymers.

BACKGROUND OF THE INVENTION

The prolonged exposure to UV radiation, such as from the sun, can lead to the formation of light dermatoses and erythemas, as well as increase the risk of skin cancers, such as melanoma, and accelerate skin aging, such as loss of skin elasticity and wrinkling.

Numerous sunscreen compositions are commercially available with varying ability to shield the body from ultraviolet light. Unfortunately, many commercial sunscreens either sting or irritate the eye. Accordingly, eye-mild sunscreen formulations are desired by the consumer.

The challenge of creating eye mild sunscreens is further magnified if one imposes additional constraints on the sunscreen composition. For example, the inventors have recognized that it would be desirable to have eye-mild, aesthetic sunscreen compositions that include a polymeric sunscreen compound (i.e., an ultraviolet radiation-absorbing polymer), and are substantially free of non-polymeric UV-absorbers.

SUMMARY OF THE INVENTION

In one aspect of the invention, a composition includes a discontinuous oil phase stabilized in a continuous water phase. The oil phase includes a UV-absorbing polymer. The composition further includes an oil-gelling polymer. The composition is substantially free of non-polymeric UV-absorbers.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. As used herein, unless otherwise indicated, all alkyl, alkenyl, and alkoxy groups may be straight or branched chain groups. As used herein, unless otherwise indicated, the term "molecular weight" refers to weight average molecular weight, (Mw).

Unless defined otherwise, all concentrations refer to concentrations by weight. Also, unless defined otherwise, the term "substantially free of," with respect to a class of ingredients refers to the particular ingredient(s) being present in a concentration less than is necessary for the particularly ingredient to be effective to provide the benefit or property for which it otherwise would be used, for example, less than about 1%, such as less than about 0.5%, for example completely free of such ingredients in certain embodiments.

UV-Absorbing Polymer

Embodiments of the invention relate to compositions including an ultraviolet radiation-absorbing polymer, (i.e., "UV-absorbing polymer"). By "UV-absorbing polymer," it is meant a polymer (a molecule that can be represented as having one or more structural units that repeat periodically, e.g., at least twice, to generate the molecule) comprising one or more UV-absorbing moieties, as discussed herein below, and that absorbs radiation in some portion of the ultraviolet spectrum (290 nm-400 nm), such as one having an extinction coefficient of at least about 1000 mol$^{-1}$ cm$^{-1}$, for example greater than 10,000 or 100,000 or 1,000,000 mol$^{-1}$ cm$^{-1}$, for at least one wavelength within the above-defined ultraviolet spectrum.

The molecular weight of the ultraviolet radiation-absorbing polymer is generally sufficiently high enough to reduce the likelihood of absorption through the skin into other body tissues, including the blood stream. In one embodiment of the invention, the molecular weight of the ultraviolet radiation-absorbing polymer is greater than about 2000, such as from about 2000 to about 1,000,000, such as from about 5000 to about 750,000, such as from about 5000 to about 500,000. In certain other embodiments, the molecular weight of the ultraviolet radiation-absorbing polymer is from about 3000 to about 200,000, such as from about 3000 to about 100,000, such as from about 3000 to about 40,000.

In order to enhance water-resistance and spreadability, the UV-absorbing polymer may, in certain embodiments, have low water solubility. For example, in certain embodiments, the UV-absorbing polymer may have a water solubility that is less than about 3% by weight, such as less than about 1% by weight. By "water solubility" it is meant the maximum weight percentage of polymer (relative to polymer plus water) that can be placed into 100 grams deionized water and agitated so that a clear solution is obtained and remains visually homogeneous and transparent at ambient temperature for 24 hours.

The UV-absorbing polymer includes one or more UV-absorbing moieties. In one particular embodiment, the first ultraviolet-absorbing moiety is a UV-A absorbing moiety By "UV-A absorbing moiety," it is meant a moiety that confers appreciable absorbance in the UV-A portion (320 nm to 400 nm) of the ultraviolet spectrum to the UV-absorbing polymer. For example, when a compound that includes the UV-absorbing polymer is cast into a film, it is possible to generate a molar extinction coefficient measured for at least one wavelength in this wavelength range of at least about 1000 mol$^{-1}$ cm$^{-1}$, such as at least about 2000 mol$^{-1}$ cm$^{-1}$, such as at least about 4000 mol$^{-1}$ cm$^{-1}$. In one embodiment, the molar extinction coefficient among at least 40% of the wavelengths in this portion of the spectrum is at least about 1000 mol$^{-1}$ cm$^{-1}$.

Examples of moieties that are UV-A absorbing include tertrahydroxybenzophenones; dicarboxydihydroxybenzophenones and alkane ester or acid halide derivatives thereof; dihydroxy-, dicarboxy-, and hydroxycarboxydibenzoylmethanes and alkane ester or acid halide derivatives thereof; dihydroxy-, dicarboxy-, and hydroxycarboxystilbenes and alkane ester or acid halide derivatives thereof; bis(hydroxystyrenyl)benzenes; bis(carboxystyrenyl)benzenes and alkane ester or acid halide derivatives thereof; dihydroxy-, dicarboxy, and hydroxycarboxycarotenes and alkane ester or acid halide derivatives thereof; 2 cyano-3,3-diphenyl acrylic acid, 2-ethyl hexyl ester; and any suitably functionalized species capable of copolymerization within the polymer chain capable of absorbing ultraviolet light in the 320-400 nm range.

In one embodiment, the UV-absorbing moiety is a UV-absorbing triazole and/or a UV-absorbing benzoylmethane. In a particularly notable embodiment, the LTV-absorbing moiety is a UV-absorbing triazole.

By "UV-absorbing triazole" it is meant a IN-absorbing moiety containing a five-member heterocyclic ring with two carbon and three nitrogen atoms. UV-absorbing triazoles include, for example, compounds of the formula (II) or (III):

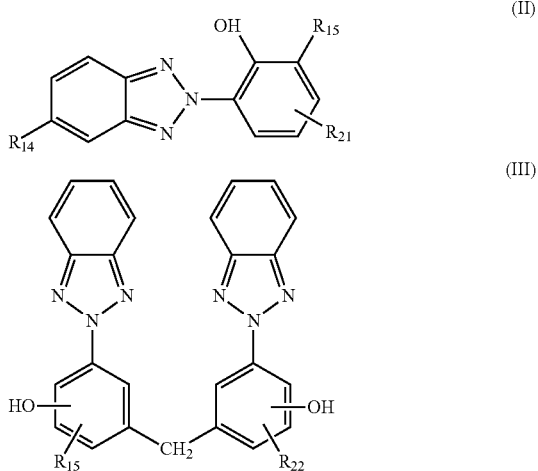

wherein $R_{14}$ is an optional $C_1$-$C_{18}$ alkyl or hydrogen; $R_{15}$ and $R_{22}$, independently, are optionally $C_1$-$C_{18}$ alkyl that may be substituted with a phenyl group, and $R_{21}$ is an optional $C_1$-$C_8$ alkyl. For (II), either of the $R_{14}$, $R_{15}$, or $R_{21}$ group may be oriented so as to be directly bonded to the (ester) linking group that connects the UV-absorbing dibenzoylmethane to the C—C backbone. For (III), either of the $R_{15}$ or $R_{22}$ group may be oriented so as to be directly bonded to the (ester) linking group that connects the UV-absorbing triazole to the C—C backbone.

UV-absorbing dibenzoylmethanes include those that may be represented by formula (IV):

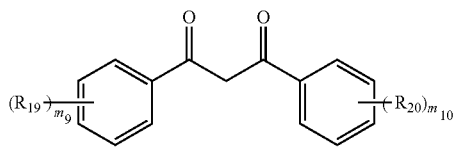

wherein $R_{19}$ and $R_{20}$, independently, are optional C1-$C_8$ alkyl or $C_1$-$C_8$ alkoxy, $m_9$ is 0 to 3, and $m_{10}$ is 1 to 3. Either of the $R_{19}$ and $R_{20}$ group may be oriented so as to be directly bonded to the (ester) linking group that connects the UV-absorbing dibenzoylmethane to the C—C backbone.

Examples and the synthesis of such non-polymeric dibenzoylmethane moieties are disclosed in U.S. Pat. No. 4,489,057 and include, but are not limited to, 4-(1,1-dimethylethyl)-4'-methoxydibenzoylmethane (avobenzone and sold as PARSOL 1789, Roche Vitamins and Fine Chemicals, Nutley, N.J., USA).

In another embodiment, the ultraviolet-absorbing moiety is a UV-B absorbing moiety. By "UV-B absorbing moiety," it is meant a moiety that confers appreciable absorbance in the UV-B portion (290 nm to 320 nm) of the ultraviolet spectrum. In one embodiment, the criteria for consideration as a UV-B absorbing moiety is similar to those described above for an UV-A absorbing moiety, except that the wavelength range is 290 nm to 320 nm.

Examples of suitable UV-B absorbing moieties include 4-aminobenzoic acid and alkane esters thereof; anthranilic acid and alkane esters thereof; salicylic acid and alkane esters thereof; hydroxycinnamic acid alkane esters thereof; dihydroxy-, dicarboxy-, and hydroxycarboxybenzophenones and alkane ester or acid halide derivatives thereof; dihydroxy-, dicarboxy-, and hydroxycarboxychalcones and alkane ester or acid halide derivatives thereof; dihydroxy-, dicarboxy-, and hydroxycarboxycoumarins and alkane ester or acid halide derivatives thereof; and other suitably functionalized species capable of copolymerization within the polymer chain.

The UV-absorbing polymer may comprise various repeat units, e.g., polyester, polyacrylate, or polysiloxane, polyamide, polyurethane, among other repeat units.

In certain particularly notable embodiments, the UV-absorbing polymer is a polyester, e.g., includes a repeat unit that includes an ester linkage. For example, the UV-absorbing polyester may have a backbone that includes a plurality of ester moieties (—COO—) that join carbon atoms within the backbone of the polymer. The structure of such a polymer may include repeat units such as (V) or (VI) below:

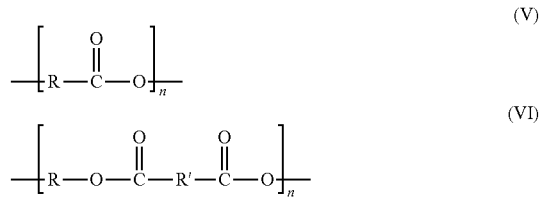

Suitable R and R' groups include alkyl, aryl, or aralkyl chains (saturated or unsaturated). In certain embodiments, the R groups include $C_2$-$C_{10}$ alkyl groups. The number of repeat units, n, may range, for example, from about 3 to about 1000, such as from about 3 to about 50, such as from 3 to about 20. A plurality of the R groups in the UV-absorbing polyester includes one or more ultraviolet-radiation absorbing moieties, as defined above.

The polyester may further include remnants of one or more comonomers, e.g., (unreacted alcohol groups, R—OH). In one embodiment of the invention, the UV-absorbing polyester includes a UV-A absorbing moiety such as a UV-absorbing triazole.

The UV-absorbing polyester may be synthesized by any of various means known to those skilled in the art, e.g., ring opening of a lactone (cyclic ester) that bears a UV-absorbing moiety; a condensation reaction of a UV-absorbing monomer having both acid and alcohol functionality (e.g. an "A-B" condensation reaction); condensing a polyol functional monomer and a polyacid functional monomer, one or both of which includes UV-absorbing moieties; and the like.

One particularly suitable UV-absorbing polyester is formed by a polycondensation reaction of the following monomers: (1) dimerdiol, $C_{36}H_{72}O$, CAS No. 147853-32-5, which is a $C_{36}$ diol; (2) di-trimethylolpropane, $C_{12}H_{26}O_5$, CAS No. 23235-61-2, which is a tetrafunctional alcohol derived from the dimerization of trimethylolpropane; (3) dimethyladipate, $C_8H_{14}O_4$, CAS No 627-93-0, the methyl ester of adipic acid; and (4) benzenepropanoic acid, 3-(2h-benzotriazol-2-yl)-5-(1,1-dimethylethyl)-4-hydroxy-, methylester, $C_{20}H_{23}N_3O_3$, CAS No 84268-33-7, a monomer that includes a UV-absorbing triazole.

In certain embodiments, the UV-absorbing polymer has the chemical structure:

-(A)$_n$-(B)$_m$-

The UV-absorbing polymer may include n moles of a first repeat unit, A; and m moles of a second repeat unit, B. As such, the ultraviolet-radiation absorbing polymer may be a copolymer that has at least two repeat units.

In certain embodiments, the UV-absorbing polymer includes a backbone of covalently bonded carbon atoms (e.g., a carbon-carbon or "C—C" backbone) from which pendant groups are attached. As will be recognized by those of skill in the art, the "backbone" refers generally to the portion of repeat units in a polymer that are covalently bonded to adjacent repeat units. If multiple such portions exist, the backbone is that portion of the polymer molecule having the largest number of continuous and covalently bonded atoms. Other smaller groups of covalently bonded atoms are considered pendant groups that branch from the backbone.

In certain embodiments, the polymer is an acrylic polymer that may be represented by the following chemical structure:

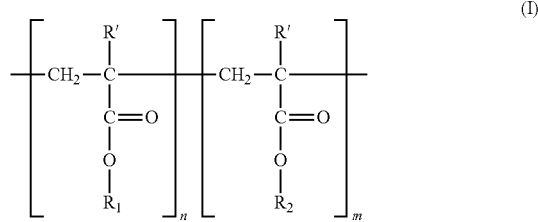

(I)

The first repeat unit, A generally includes first pendant group, $R_1$ which is linked to the C—C backbone via, for example, a linking group, e.g., an ester linking group (ester linking groups are shown in the chemical structure above) where the first pendant group, $R_1$, includes a first ultraviolet-radiation absorbing moiety. The first ultraviolet-absorbing moiety absorbs in the ultraviolet spectrum.

Acrylic polymers suitable for use in the present invention may be synthesized, for example by methods known in the art. For example, suitable polymers may be formed by addition polymerization, such as via free-radical addition polymerization of suitable ethylenically unsaturated monomers. The resulting polymer may have its repeat units alternating, block, random, graft, star or other configurations.

For example, a first ethylenically unsaturated compound (monomer) that includes an ultraviolet-absorbing moiety, may be reacted with a second ethylenically unsaturated compound (monomer) that includes, for example in one embodiment, at least one siloxane linkage. In another embodiment, the second ethylenically unsaturated monomer includes a hydrocarbon moiety, such as a hydrocarbon moiety having an intermediate number of carbon atoms. This reaction may take place in the presence of an initiator such as AIBN or other suitable initiators. In one embodiment, the first ethylenically unsaturated compound includes a UV-A absorbing moiety. The UV-A absorbing moiety may be a benzotriazole. One such suitable benzotriazole monomer is 2' hydroxy-5'-methacryloxyethylphenyl)-2H-benzotriazol.

In one embodiment, the UV-absorbing polymer includes at least one siloxane (Si—O—Si) linkage in the backbone. In one embodiment, the backbone has about 10 or more siloxane linkages, such as about 50 or more siloxane linkages. In one embodiment, the second UV-absorbing polymer is a dimethicodiethyl benzal malonate, also known as a benzylidene malonate silicone, such as the filter known as "Polysilicone-15." Examples of suitable benzylidene malonate silicone include those described in U.S. Pat. No. 6,193,959 to Bernasconi et al. A particularly suitable benzylidene malonate includes "Parsol SLX," commercially available from DSM (Royal DSM N.V.) of Heerlen, Netherlands.

In another embodiment, the second UV-absorbing polymer includes 2-cyano-3,3-diphenyl acrylic acid functional groups, such as are present in those polymeric sunscreens disclosed in U.S. Pat. No. 6,962,692; U.S. Pat. No. 6,899,866; and/or U.S. Pat. No. 6,800,274; including hexanedioic acid, polymer with 2,2-dimethyl-1,3-propanediol, 3-[(2-cyano-1-oxo-3,3-diphenyl-2-propenyl)oxy]-2,2-dimethylpropyl 2-octyldodecyl ester; sold under the trade name "POLYCRYLENE," commercially available from the HallStar Company of Chicago, Ill.

The UV-absorbing polymers useful in the present invention may, in certain embodiments, be "rich" in ultraviolet-absorbing moieties. As such they are highly suitable for formulation into topical sunscreens. By "rich" in ultraviolet-absorbing moieties, it is meant that at least 10% by of the weight percentage of the polymer is attributable to the UV-absorbing moiety.

It is further desirable that the UV-absorbing polymer have an absorbance in the UV that is sufficiently high so as to make it suitable for use as a sunscreen for the human body. In one embodiment, the polymer, when dissolved in a suitable solvent (e.g., DMSO, ethyl acetate, tetrahydrofuran, or the like) and spread or cast into a thin film, has a molar extinction coefficient measured for at least one wavelength within the UV spectrum, such as in the UV-A spectrum, of at least about 1000 mol$^{-1}$ cm$^{-1}$, such as at least about 2000 mol$^{-1}$ cm$^{-1}$, such as at least about 4000 mol$^{-1}$ cm$^{-1}$, or even 10,000 or 100,000 or 1,000,000 mol$^{-1}$ cm$^{-1}$.

Topical Composition

In one embodiment, a composition suitable for topical/cosmetic use for application to the human body (e.g., keratinaceous surfaces such as the skin or hair), especially the skin, is provided. The composition includes one or more UV-absorbing polymer described herein. The concentration of the UV-absorbing polymer may vary from 0.001% to about 50% by weight, such as from about 0.1% to about 50%, such as from about 0.5% to about 40% of the composition. In certain embodiments the concentration of UV-absorbing polymer is about 10% or more, such as from about 11% to about 30%, such as from about 11% to about 25%, such as from about 11% to about 20%.

According to certain embodiments of the invention, compositions of the present invention are substantially free of non-polymeric UV-absorbers. Furthermore, if all UV-absorbing polymers were removed from certain embodiments of compositions of the present invention, the resulting composition would have an SPF, as determined via a suitable in-vivo test method, of 2 or less.

A suitable in-vivo test method is the "Colipa Method," known to those skilled in the art. In this method, the minimum dose of solar-simulated ultraviolet radiation (UVR) required to induce a minimally perceptible erythema on human skin is determined for untreated skin and for the skin treated with the composition (erythema readings taken 24 hours after irradiation). The ratio of the dose of UV radiation needed to induce minimally perceptible erythema for the composition-protected skin (MEDp), divided by the dose required for a minimally perceptible erythema for unprotected skin (MEDu) results in the SPF value of the composition.

An irradiation apparatus used for SPF determinations is, for example, a Multiport Solar Simulator Model 601 (Solar Light Co., Philadelphia, Pa., USA) which consists of a 300 W Xenon lamp filtered with a UG11 1 mm thick filter and a WG320 1 mm filter (Schott Co., Philadelphia, Pa., USA) to allow exposure to UV between 240 and 800 nanometers.

"UV-screening compounds" that the composition is substantially free of may be limited to (a) non-polymeric UV-absorbers, typically characterized as "organic" (include predominantly or only atoms selected from carbon, hydrogen, oxygen, and nitrogen) and having no definable repeat unit and typically having molecular weights that are about 600 daltons or less, such as about 500 daltons or less, such as less than 400 daltons. Examples of such compounds, sometimes referred to as "monomeric, organic UV-absorbers" include, but are not limited to: methoxycinnamate derivatives such as octyl methoxycinnamate and isoamyl methoxycinnamate; camphor derivatives such as 4-methyl benzylidene camphor, camphor benzalkonium methosulfate, and terephthalylidene dicamphor sulfonic acid; salicylate derivatives such as octyl salicylate, trolamine salicylate, and homosalate; sulfonic acid derivatives such as phenylbenzimidazole sulfonic acid; benzone derivatives such as dioxybenzone, sulisobenzone, and oxybenzone; benzoic acid derivatives such as aminobenzoic acid and octyldimethyl para-amino benzoic acid; octocrylene and other $\beta,\beta$-diphenylacrylates; dioctyl butamido triazone; octyl triazone; butyl methoxydibenzoyl methane; drometrizole trisiloxane; and menthyl anthranilate.

In another embodiment of the invention, UV-screening compounds that the composition is substantially free of also may include (b) ultraviolet-screening particles, ("UV-screening particles") typically used at least in part to scatter ultraviolet radiation. Examples include inorganic oxides including titanium dioxide, zinc oxide, iron oxides, silicone oxides, or other metal (e.g., transition metal, such as crystalline transition metal) oxides. Such ultraviolet screening particles are typically solid particles having a diameter from about 0.1 micron to about 10 microns.

For purposes of clarity, and as one skilled in the art will readily appreciate, specifically excluded from the definition of "UV-screening compounds" are UV-absorbing polymers, as defined above.

As discussed above, in certain embodiments, the composition is substantially free of any UV-screening compounds (i.e., substantially free of (a) non-polymeric UV-absorbers and substantially free of (b) UV-screening particles. In certain alternative embodiments, the composition is substantially free of (a) non-polymeric UV-absorbers, but the composition includes (b) UV-screening particles. In particular, in certain alternative embodiments, the composition is substantially free of (a) non-polymeric UV-absorbers, but includes titanium dioxide and/or zinc oxide.

The compositions useful in the present invention may be used for a variety of cosmetic uses, especially for protection of the skin from UV radiation. The compositions, thus, may be made into a wide variety of delivery forms. These forms include, but are not limited to, suspensions, dispersions, solutions, or coatings on water soluble or water-insoluble substrates (e.g., substrates such as organic or inorganic powders, fibers, or films). Suitable product forms include lotions, creams, gels, sticks, sprays, ointments, mousses, and compacts/powders. The composition may be employed for various end-uses, such as recreation or daily-use sunscreens, moisturizers, cosmetics/make-up, cleansers/toners, anti-aging products, or combinations thereof. The compositions of the present invention may be prepared using methodology that is well known by an artisan of ordinary skill in the field of cosmetics formulation.

In certain embodiments, compositions of the present invention include water and are thus "aqueous compositions." In certain further embodiments, the composition includes a water phase and an oil phase. In certain other embodiments, the composition includes a continuous water phase in which a discontinuous oil phase that includes the UV-absorbing polymer is stabilized. In certain embodiments, the UV-absorbing polymer is dissolved, as opposed to being dispersed or suspended, within the oil phase. The oil phase may, in turn, be stabilized within the water phase. The oil phase may be such that it is present in discrete droplets or units having an average diameter of about one micron to about 1000 microns, such as from about 1 micron to about 100 microns.

For embodiments in which the composition includes a water phase and an oil phase, the relative concentrations of water phase and oil phase may be varied. In certain embodiments the percentage by weight of water phase is from about 10% to about 90%, such as from about 40% to about 80%, such as from 50% to about 80%; wherein the balance is oil phase.

The percentage of water included in the compositions may range from 20% to about 90%, such as from about 20% to about 80%, such as from about 30% to about 70%, such as greater than about 50%, such as from about 51% to about 80%, such as from about 51% to about 70%, such as from about 51% to about 60%.

In certain embodiments the composition may include one or more compounds suitable for enhancing photostability. Photostabilizers include, for example, diester or polyesters of a naphthalene dicarboxylic acid.

Carrier

The one or more UV-absorbing polymers in the composition may be combined with a "cosmetically-acceptable topical carrier," i.e., a carrier for topical use that is capable of having the other ingredients dispersed or dissolved therein, and possessing acceptable properties rendering it safe to use topically. As such, the composition may further include any of various functional ingredients known in the field of cosmetic chemistry, for example, emollients (including oils and waxes) as well as other ingredients commonly used in personal care compositions such as humectants, thickeners, opacifiers, fragrances, dyes, solvents for the UV-absorbing polymer, among other functional ingredients. Suitable examples of solvents for the UV-absorbing polymer include dicaprylyl carbonate available as CETIOL CC from Cognis Corporation of Ambler, Pa. In order to provide pleasant aesthetics, in certain embodiments of the invention, the composition is substantially free of volatile solvents, and, in particular $C_1$-$C_4$ alcohols such as ethanol and isopropanol.

Furthermore, the composition may be substantially free of ingredients that would render the composition unsuitable for topical use. As such, the composition may be substantially free of solvents such as volatile solvents, and, in particular, free of volatile organic solvents such as ketones, xylene, toluene, and the like.

Emulsifiers

In certain embodiments of the invention, the composition is substantially free of low molecular weight emulsifiers. By "emulsifier," it is meant any of a variety of molecules that are suitable for emulsifying discrete oil-phase droplets in a continuous water phase or vice-versa. By "low molecular weight emulsifiers," it is meant emulsifiers having a molecular weight of about 2000 daltons or less, such as about 1000 daltons or less.

In certain embodiments, the compositions are substantially free of low molecular weight oil-in-water (O/W) emulsifiers. By O/W emulsifiers, it is meant, emulsifiers that can form, when mixed either lightly or vigorously, in a 1% by weight concentration with pure deionized water, a mixture that is visibly homogeneous as well as being clear or translucent. The mixture is such that at all wavelengths between 400 and 700 nm, it has a ratio of transmitted light intensity to incident light intensity that is about 10% or more, for a path length of 1 cm. By "visibly homogeneous," it is meant that the mixture is not characterized by an evident "layering" or flotation or phase separation. O/W emulsifiers may be capable of lowering the surface tension of pure deionized water to 45 dynes per centimeter when added to pure deionized water to a concentration of O/W emulsifier of 0.5% or less at room temperature. O/W emulsifiers are sometimes characterized as having a hydrophilic-lipophilic balance (HLB) that is about 8 or more, such as about 10 or more.

In certain embodiments, the composition is substantially free of the following classes of anionic, non-ionic, amphoteric, and cationic emulsifiers:

(I) anionic emulsifiers: alkyl, aryl or alkylaryl, or acyl-modified versions of the following moieties: sulfates, ether sulfates, monoglyceryl ether sulfates, sulfonates, sulfosuccinates, ether sulfosuccinates, sulfosuccinamates, amidosulfosuccinates, carboxylates, amidoethercarboxylates, succinates, sarcosinates, amino acids, taurates, sulfoacetates, and phosphates;

(II) nonionic emulsifiers: ethoxylates of alcohols, amides, monoglycerides; sorbitan esters; polyoxyethylene derivatives of polyol esters; alkyl glucosides or polyglucosides; polyglyceryl esters; noncrosslinked silicone copolymers such as alkoxy or alkyl dimethicone copolyols, silicones having pendant hydrophilic moieties such as linear silicones having pendant polyether groups or polyglycerin groups; crosslinked elastomeric solid organopolysiloxanes comprising at least one hydrophilic moieties: polyethylene glycol, polypropylene glycol or polyglyceryl esters; Note that specifically excluded from this list of non-ionic emulsifiers are fatty alcohols (defined below).

(III) amphoteric emulsifiers: alkyl betaines, amidoalkyl betaines, alkylamphoacetates; amidoalkyl sultaines; amphophosphates; phosphorylated imidazolines; carboxyalkyl alkyl polyamines; alkylimino-dipropionates alkylamphoglycinates (mono or di); alkylamphopropri-onates; N-alkyl β-aminoproprionic acids; alkylpolyamino carboxylates; and (IV) cationic emulsifiers: alkyl quaternaries, benzyl quaternaries, ester quaternaries, ethoxylated quaternaries, and alkyl amines.

In another embodiment, the composition is substantially free of anionic, non-ionic, amphoteric, and cationic emulsifiers, and is also substantially free of certain (V) polymeric emulsifiers: copolymers based on acrylami-doalkyl sulfonic acid such as Aristoflex® AVC and Aristoflex® HMB by Clariant Corporation; and Granthix APP by Grant Industries, Inc.

In certain embodiments of the invention, compositions of the present invention include a film forming polymer. By "film-forming polymer," it is meant a polymer that when dissolved, emulsified, or dispersed in one or more diluents, permits a continuous or semi-continuous film to be formed when it is spread with a liquid vehicle onto smooth glass, and the liquid vehicle is allowed to evaporate. As such, the polymer should dry on the glass in a manner in which over the area which it is spread should be predominantly continuous, rather than forming a plurality of discrete, island-like structures. Generally, the films formed by applying compositions on the skin according to embodiments of the invention described herein, are less than, on average, about 100 microns in thickness, such as less than about 50 microns.

In contrast to polymeric UV-absorbing polymers, film-forming polymers generally do not absorb ultraviolet radiation and therefore do not meet the requirements for UV-absorbing polymers.

Film-forming polymers may be useful in compositions of the present invention in that they may enhance the UV-protection (UV-A, UV-B or both) of the composition and/or enhance the waterproofing or water resistance of the composition.

Suitable film-forming polymers include natural polymers such as polysaccharides or proteins and synthetic polymers such as polyesters, polyacrylics, polyurethanes, vinyl polymers, polysulfonates, polyureas, polyoxazolines, and the like. Specific examples of film-forming polymers include, for example, hydrogenated dimer dilinoleyl/dimethylcarbonate copolymer, available from Cognis Corporation of Ambler, Pa. as COSMEDIA DC; copolymer of vinylpyrrolidone and a long-chain a-olefin, such as those commercially available from ISP Specialty Chemicals of Wayne, N.J. as GANEX V220; vinylpyrrolidone/tricontanyl copolymers available as GANEX WP660 also from ISP; water-dispersible polyesters, including sulfopolyesters such those commercially available from Eastman Chemical as EASTMAN AQ 38S. The amount of film-forming polymer present in the composition may be from about 0.1% to about 5%, or from about 0.1% to about 3%, or from about 0.1% to about 2%.

In certain embodiments, the composition includes an oil-gelling polymer that may serve to suspend an oil phase in a continuous water phase without the requirement of using a low molecular weight emulsifier. By "oil-gelling polymer," it is meant a polymer that is capable of forming a gel with mineral oil at 25° C. In particular when the oil-gelling polymer is mixed with mineral oil to a concentration of oil-gelling polymer that is between about of 0.25% to 2.0% by weight, the resulting mixture has a yield stress of about 5 pascals (Pa) or more, such as about 10 Pa or more, such as from about 10 Pa to about 1100 Pa. Particularly suitable oil-gelling polymers are $C_2$-$C_4$ alkylcellulose polymers, such as ethylcellulose, which is an ethyl ether of cellulose comprising a long-chain polymer consisting of anhydroglucose units joined together by acetal linkages. Other examples of oil-gelling polymers are dibutyl ethylhexanoyl glutamide and dibutyl lauroyl glutamide (available as EP-21 and GP-1 from Ajinomoto USA of Fort Lee, N.J.).

A suitable method to determine yield stress is the following: place samples to be tested in a water bath set at 25° C. for a period time sufficient to allow the sample to equilibrate (at least about an hour). Gently place about 1.0 grams of the composition to be tested on the base plate of a properly calibrated rheometer (e.g., Advanced Rheometer AR 2000) having a 20 mm cone with a 1 degree angle, a 20 mm plate, a water bath, and a solvent trap. The sample size should be just sufficient to allow some minor flow of the sample out of the gap once the final position of the cone and plate is reached (0.030 mm). To minimize shearing of the sample prior to testing, each sample should be applied to the plate in a consistent manner, by gently scooping out the sample in one motion without significant shear or spreading, evenly layered on the plate, and without compressing and rotating the spatula away from the sample. The sample is centered on the base plate and laid relatively even across the plate. Once the measurement position is reached, a small bulge of the sample material protrudes from the gap. This is removed quickly and gently so as not to disturb the top plate and pre-shear the sample. The instrument is set for a controlled shear rate run (log) with a shear rate spanning from, for example, $0.01^{-1}$, to $300^{-1}$; 300 data points collected; 300 seconds test duration; 25° C. water bath. The output device attached to the rheometer is set to plot stress (Pa) as a function of shear rates$^{-1}$. Yield stress is determined from the plot of yield stress versus shear rate as the stress at which the curve departs from linearity. The average and standard deviation of the 3 runs is determined.

The concentration of oil-gelling polymer in the composition may be an amount sufficient to stabilize the composition from phase separation (that would otherwise occur if the oil-gelling polymer were not present in the composition) within a time period of one month when maintained at 20° C.-25° C. In certain embodiments, the concentration of oil-gelling polymer is from about 0.025% to about 2%, such as from about 0.05% to about 1%, such as from about 0.1% to about 0.4%.

Furthermore, in certain embodiments the composition includes a water-gelling polymer. By "water-gelling polymer," it is meant a polymer that is capable of forming a gel with deionized water. In particular, when the water-gelling polymer is mixed with deionized water to a concentration of water-gelling polymer that is between about 0.25% to 2.0% by weight, the resulting mixture has a yield stress of about 5 pascals (Pa) or more, such as about 10 Pa or more, such as from about 10 Pa to about 1100 Pa.

Examples of suitable water-gelling polymers include any variety of associative polymers that have water-soluble groups as well as hydrophobic modification. Examples include vegetable gums such as pectin, carageenan, xanthan gum, sclerotium gum and the like; polyvinylpyrrolidone; cellulose polymer, and acrylic polymers. Particularly notable are xanthan gum, available as KELTROL from CP Kelco of Copenhagen, Denmark; AMIGEL, a homopolysaccharide gum obtained from fermenting *Sclerotium rolfsii* and commercially available from Alban Muller/Tri-K of France; hydrophobically modified-acrylic polymers such as CARBOPOL polymers available from Noveon of Cleveland, Ohio; polyethylene glycol esters such as PEG-150 distearate which is available from the Stepan Company of Northfield, Ill. or from Comiel, S.p.A. of Bologna, Italy under the tradename, "PEG 6000 DS;" and water-soluble cellulose polymers such as hydroxypropylmethylcellulose, carboxymethylcellulose, hydroxypropylcellulose, polyvinylpyrrolidone, methylcellulose and sodium ethylcellulose sulfate. The concentration of water-gelling polymer in the composition may be from about 0.05% to about 2%, such as from about 0.1% to about 1%, such as from about 0.1% to about 0.5%.

In certain embodiment, the composition includes a fatty alcohol. By fatty alcohol, it is meant any of various saturated or unsaturated, linear or branched, $C_7$-$C_{22}$ unethoxylated, aliphatic alcohols, such as those having a single —OH group. The fatty alcohol may be derived from plant or animal oils and fats having at least one pendant hydrocarbon-comprising chain. The fatty alcohol may have from 9 to about 15 carbon atoms, such as from about 11 to about 15 carbon atoms. Examples of unbranched fatty alcohols include cetyl alcohol and stearyl alcohol. Suitable branched fatty alcohols may comprise one or more branches in the carbon backbone of the molecule. An example of a suitable branched fatty alcohol is isostearyl alcohol. Other suitable branched fatty alcohols include monobranched fatty alcohols, e.g. ISALCHEM 123, available from Sasol Chemical Co of Bad Homburg, Germany. The concentration of fatty alcohol in the composition may be from about 0.5% to about 5%, such as from about 1% to about 4%, such as from about 1.5% to about 3%.

In certain embodiments, the composition includes an emollient. Emollient refers to materials used for the prevention or relief of dryness, as well as for the protection of the skin. Suitable emollients include mineral oils, petrolatum, vegetable oils (glyceryl esters of fatty acids, triglycerides), waxes and other mixtures of fatty esters, not necessarily esters of glycerol (e.g., isopropyl palmitate, isopropyl myristate), and silicone oils such as dimethicone. One notable class of emollient which also serves to thicken the oil phase of the composition includes fatty acid esters of butylene or propylene glycol, such as butylene glycol cocoate available from Gattefosse of Paris, France. One particularly suitable butylene glycol cocoate, also available from Gattefosse, is a mixture of cocoate mono and di-esters of butylene glycol mixed with isostearyl alcohol (fatty alcohol), and ethyl cellulose (an oil-gelling polymer). This mixture is sold as "EMULFREE CBG."

In certain embodiments, the composition includes a UV-absorbing polymer and is substantially free of non-polymeric UV-absorbers and, in certain embodiments, substantially free of any UV-screening compounds, and is substantially free of low molecular weight emulsifiers. In certain embodiments, the composition desirably includes both an oil phase that includes the oil-gelling polymer and fatty alcohol, and a water phase that includes the water-gelling polymer. The oil phase may optionally include emollient such as a fatty acid ester of butylene glycol.

The compositions of the present invention may further comprise one or more other cosmetically active agent(s). A "cosmetically active agent" is a compound that has a cosmetic or therapeutic effect on the skin, e.g., agents to treat wrinkles, acne, or to lighten the skin. The cosmetically active agent will typically be present in the composition of the invention in an amount of from about 0.001% to about 20% by weight of the composition, e.g., about 0.01% to about 10% such as about 0.1% to about 5% by weight of the composition.

In certain embodiments the composition has a pH that is from about 4.0 to about 8.0, such as from about 5.5 to about 7.0.

Compositions of the present invention have low tendency to irritate the eyes and, in certain embodiments, the skin as well. Low tendency to irritate eyes may be measured using, for example, the Epi-Ocular Test as set forth below. A higher EPI-OCULAR value of a composition tends to indicate less irritation to the eyes associated therewith as compared to a composition having a lower EPI-OCULAR value, which composition tends to cause higher levels of irritation to the eyes.

Applicants have recognized that the present compositions having surprisingly high EPI-OCULAR values/lower irritation associated therewith. For example, in certain embodiments, the compositions have an EPI-OCULAR value of about 10 or greater. In certain other embodiments, the compositions exhibit an EPI-OCULAR value of about 12 hours or greater, such as about 15 hours or greater, such as about 20 hours or greater, such as about 24 hours or greater.

The compositions of the present invention may be prepared using mixing and blending methodology that is well known by an artisan of ordinary skill. In one embodiment of the invention, a method of making a composition of the present invention includes preparing an oil phase by mixing at least the UV-absorbing polymer with oil-gelling polymer and a fatty alcohol; and preparing a water phase, by mixing at least water and water-gelling polymer. The oil phase and the water phase may then be mixed in a manner sufficient to disperse the oil phase in the water phase such that the water phase is continuous and the oil phase discontinuous.

The compositions of the present invention can be used by topically administering to a mammal, e.g., by the direct laying on, wiping or spreading of the composition on the skin or hair of a human.

The following EPI-OCULAR test is used in the instant methods and in the following Examples. In particular, as described above, the EPI-OCULAR test is used to determine when a composition has reduced eye irritation according to the present invention.

Epi-Ocular® Test:

The potential for irritation to the eyes expected for a given formulation is measured in accordance with the "Epi-Ocular® Test" as set forth below. The Epi-Ocular Test is a cell based in-vitro assay in which cell viability is assessed by measuring the activity of cell enzymes that can reduce MTT (3-(4,5-Dimethylthiazol-2-yl)-2,5-diphenyltetrazolium bromide). The exposure time required for a 50% decrease in the viability of the cells in a 3-D scaffold is reported as the EPI-OCULAR VALUE for the composition. An EPI-OCULAR VALUE>10 hours is considered to be particularly mild, while an EPI-OCULAR VALUE >24 hours is even more desirable.

EpiOcular® OCL-200 tissue (differentiated human epidermal keratinocytes) and assay media are provided by MatTek Corporation of Ashland, Mass. The tissues are stored at 2-8° C. until ready for use. On the day of testing, the tissues are warmed to 37° C. in 1 ml of fresh media. Duplicate tissues are dosed topically with 100 microliters of test composition, positive control (0.3% Polyethylene glycol octylphenyl ether, CAS No. 9002-93-1. available from Fisher Scientific Fairlawn, N.J.), or negative control (sterile water). Tissues are incubated for 24 hours, then removed and rinsed with phosphate buffer solution, incubated for ten minutes at room temperature in fresh media, then placed in a 24-well plate containing 0.3 ml of 1 mg/mL of MTT in MTT Addition Medium supplied by MatTek and incubated in the dark for approximately 3 hours. Following incubation with MTT, the medium is decanted and the reduced intracellular MTT is extracted from each tissue construct using 2 ml of isopropanol and orbital shaking at room temperature for 2 hours. Two hundred microliter aliquots of the extract solution are transferred to a 96-well plate and read on a plate reader for optical density at 540-550 nm. Percent Viability for each exposure time point is calculated by dividing mean optical density (OD) of the test material by that of the negative control, where the negative control represents 100% viability, and multiplying the result by 100. Percent Viability is plotted versus time on a semi-log scale and exposure time required for a 50% decrease in cell viability (i.e., $ET_{50}$, or "EPI-OCULAR VALUE") is extrapolated from the plot. The test is considered valid if 1) the positive control causes an $ET_{50}$ within two deviations of the historical mean and 2) the mean optical density of the negative control at the shortest and longest time points are within 20%.

Additional details of the test are described in the following publication: McCain, N. E., Binetti, R. R., Gettings, S. D., Jones, B. C. Cell Biology & In Vitro Toxicology, Avon Products, Inc., Suffern, N.Y. The Toxicologist, 66 (1-S), 243, Soc. of Toxicol. (Reston, Va.) which is incorporated herein by reference.

EXAMPLES

The following examples illustrate the preparation and efficacy of compositions of the present invention.

Example I

The following example illustrates the low eye irritation of certain compositions of the present invention. Inventive compositions E1 and E2, which include a UV-absorbing polymer and an oil-gelling polymer, and which are substantially free of UV-screening compounds and low molecular weight emulsifiers; and E-3, which includes a UV-absorbing polymer, an oil-gelling polymer and UV-screening particles, and which is substantially free of non-polymeric UV-absorbers and low molecular weight emulsifiers, were prepared as shown in Table 1 and described below.

TABLE 1

| INGREDIENT | WEIGHT PERCENTAGE | | |
|---|---|---|---|
| | E1 | E2 | E3 |
| Water | 62.30 | 62.30 | 60.30 |
| AMIGEL | 0.4 | 0.4 | 0.4 |
| PHENONIP XB | 1 | 1 | 1 |
| PEMULEN TR-2 | 0.3 | 0.3 | 0.3 |
| EMULFREE CBG | 6 | 6 | 6 |
| Polymeric Sunscreen 1 | 15 | | 15 |
| Polymeric Sunscreen 2 | | 15 | |
| CETIOL CC | 15 | 15 | 15 |
| TiO2 | | | 2 |

AMIGEL is sclerotium gum, available from Alban Muller International of Hialeah, Fla. PHENONIP XB is phenoxyethanol (and) methylparaben (and) ethylparaben (and) propylparaben, available from Clariant of Muttenz, Switzerland. PEMULEN TR-2 is Acrylates/$C_{10-30}$ Alkyl Acrylate Crosspolymer, available from Noveon/Lubrizol of Wickliffe, Ohio. EMULFREE CBG is Isostearyl Alcohol (and) Butylene Glycol Cocoate (and) Ethylcellulose, available from Gattesfosse of France. CETIOL CC is Dicaprylyl Carbonate, available from Cognis, now BASF of Ludwigshafen, Germany. Neo-HELIOPAN is available from Symrise of Teterboro, N.J. PARSOL 1789 is available from DSM. UVINUL M40 is available from BASF of Ludwigshafen, Germany. CORO-PAN TQ is available from Hallstar Company of Chicago, Ill.

Polymeric Sunscreen 1 is a UV-absorbing polyester that was prepared by polycondensation reaction of the following monomers: (1) dimerdiol, $C_{36}H_{72}O$, (2) di-trimethylolpropane, $C_{12}H_{26}O_5$, (3) dimethyladipate, and (4) benzenepropanoic acid, 3-(2h-benzotriazol-2-yl)-5-(1,1-dimethylethyl)-4-hydroxy-, methylester, $C_{20}H_{23}N_3O_3$. The mole ratio of the four monomers (monomer 1:monomer 2:monomer 3:monomer 4 was 2.4:3.1:4.0:8.0. The molecular weight was estimated to be about 6800.

Polymeric Sunscreen 2 was a UV-absorbing polymer similar to Polymeric Sunscreen 1, except that the mole ratio of the four monomers (monomer 1: monomer 2: monomer 3: monomer 4 was 3.4:2.1:4.0:6.0. The molecular weight was estimated to be about 6400.

Inventive Examples E1-E3 were made by the following process:

A water phase was prepared by adding water to a main vessel and heating to 70° C.-75° C. with mixing (500-750) RPM. AMIGEL was added and mixed until dissolved. PHENONIP was added and mixed until dissolved. PEMULEN was added slowly and mixed until uniform. An oil phase was prepared by charging a vessel with Cetiol CC and mixing. Heat was applied. At 60° C. the UV-absorbing polymer was added. EMULFREE CBG was added, and mixing was continued for 5 minutes and mixture was heated to 70° C.-75° C. At 70° C.-75° C., the oil phase was added to the water phase with moderate shear (650-900) RPM. The pH was adjusted to 6.5 with sodium hydroxide, and mixing was continued. The mixture was allowed to slowly cool to room temperature. At 60° C., mixing was reduced to a speed of 400-600 RPM.

In addition to the Inventive Examples E1-E3, a Comparative Example, C1 was prepared as shown in Table 2 and described below.

TABLE 2

| INGREDIENT | WEIGHT PERCENTAGE |
|---|---|
| Purified Water | 42 |
| NaCL USP | 1 |
| PHENONIP XB | 1 |
| TINOSORB M | 3 |
| DISPERSUN OL-300 | 0.7 |
| CETIOL CC | 20 |
| ZCOTE HP1 | 20 |
| Micro Titanium Dioxide MT-100TV | 2 |
| CRODACOL C-95, NF | 0.5 |
| Abil We 09 | 3 |
| EMERSOL 312 | 1 |
| Magnesium Stearate | 1.8 |
| PARASOL SLX | 4 |

DISPERSUN OL-300 is Polyhydroxystearic Acid, available from Innospec of Edison, N.J. ZCOTE HPI is zinc oxide, available from BASF of Ludwigshafen, Germany. MT-100TV is available from Presperse of Somerset, N.J. EMERSOL 312 is linoleic acid. TINOSORB M is 2,4-Bis{[4-(2-ethyl-hexyloxy)-2-hydroxyl]-phenyl}-6-(4-methoxyphenyl)-(1,3,5)-triazine, available from Ciba Specialty Chemicals of Basel, Switzerland. ABIL WE09 is Polyglyceryl-4-Isostearate, available from Evonik Industries of Darmstadt, Germany. PARSOL SLX is Polysilicone-15, available from DSM. CRODACOL is cetyl alcohol, available from Croda of Edison, N.J.

Comparative Example C1 was made by the following process:

A water phase was prepared by adding water and sodium chloride to a main vessel. PHENONIP was added and mixed until dissolved. TINOSORB was added slowly and mixed until homogeneous. The mixture was heated to 75° C. An oil phase was prepared by charging a vessel with Cetiol CC and mixing. DISPERSUN was pre-heated and added and slowly mixed until uniform. The mixture was heated and zinc oxide and titanium dioxide were slowly added until uniform. Once uniform, the mixture was homogenized for 10 minutes and heated to 75° C. CRODACOL, magnesium stearate, ABIL WE09, and EMERSOL were added with mixing at 800 rpm until uniform. PARSOL SLX was then added and mixed at 800 rpm until uniform, then the speed was reduced to 400 rpm. The water phase was added to a main tank, with both phases at 75° C. and at 800 rpm mixing speed. After mixing the phases until homogeneous, they were continued to mix at 400-800 rpm and then cooled to 35° C., homogenized for 10 minutes, returned to slow mixing and allowed to cool to room temperature.

The EPI-OCULAR VALUES of Inventive Examples E1-E3 and Comparative Example C1 were determined using the Epi-Ocular Test as described above and the results reported in Table 3.

TABLE 3

| Example | EPI-OCULAR VALUE |
|---|---|
| E1 | >24 hrs |
| E2 | >24 hrs |
| E3 | >24 hrs |
| C1 | 11.2 hrs |

The EPI-OCULAR Values indicate that the inventive examples (which have UV-absorbing polymer, are substantially free of non-polymeric UV-absorbers, include an oil-gelling polymer, and are substantially free of low molecular weight emulsifiers) have very high EPI-OCULAR VALUES. In contrast, the comparative composition C1 has a much lower EPI-OCULAR VALUE. Comparative Example C1, which has an EPI-OCULAR VALUE to "pass" the test, but is still less than half that of the inventive examples, has UV-absorbing polymer, but is not substantially free of non-polymeric UV-absorbers, has no oil-gelling polymer, and is not substantially free of low molecular weight emulsifiers.

Example II

Inventive Examples E1 and E2 were tested for sun protection factor, using the following IN-VITRO SPF TEST METHOD. The baseline transmission of a PMMA plate (substrate) without application of any test materials applied thereto was measured. Test samples were prepared by providing a sample of polymer. (Blends may also be tested by this method. The polymer(s) can be tested without any additional additives; with a solvent system, or as a part of a personal care composition that may include solvent and/or additional ingredients.)

Each sample was separately applied to a PMMA plate (available from Helioscience, Marseille, France) using an application density of 2 micro liters of solution per square centimeter of substrate, rubbing in into a uniform thin layer with the operator's finger, and allowed to dry. Three such samples were done for each test material. The samples were then allowed to dry for 15 minutes before measurement of absorbance using calibrated Labsphere® UV-1000S UV transmission analyzer (Labsphere, North Sutton, N.H., USA). The absorbance measures were used to calculate SPF and PFA indices (biological protection factor in the UVA based).

SPF and PFA were calculated using methods known in the art—see equation (1) below for calculation of SPF:

$$SPF_{in\ vitro} = \frac{\int_{\lambda=290\ nm}^{\lambda=400\ nm} E(\lambda) * I(\lambda) * d\lambda}{\int_{\lambda=290\ nm}^{\lambda=400\ nm} E(\lambda) * I(\lambda) * 10^{-A_0(\lambda)} * d\lambda} \quad (1)$$

where:
$E(\lambda)$=Erythema action spectrum
$I(\lambda)$=Spectral irradiance received from the UV source
$A_0(\lambda)$=Mean monochromatic absorbance of the test product layer before UV exposure
$d\lambda$=Wavelength step (1 nm)

Using the method described above, Inventive Examples E1 and E2 were determined to have an SPF of 22 and 37 respectively.

It is understood that while the invention has been described in conjunction with the detailed description thereof, that the foregoing description is intended to illustrate and not limit the scope of the invention.

The invention claimed is:

1. A composition comprising: a continuous water phase; a discontinuous oil phase comprising a UV-absorbing polyester that is formed by a polycondensation reaction of dimerdiol (monomer 1), di-trimethylolpropane (monomer 2), dimethyladipate (monomer 3) and benzenepropanoic acid (monomer 4), in an amount effective to provide said composition with an SPF of about 2 or more in the absence of a UV-screening compound, wherein the mole ratio of the four monomers (monomer 1: monomer 2: monomer 3: monomer 4) is selected from the group consisting of 2.4:3.1:4.0:8.0 and 3.4:2.1:4.0:6.0; wherein said discontinuous oil phase is stable in said continuous water phase; and an oil gelling polymer, wherein said composition is substantially free of a non-polymeric UV-absorber.

2. The composition of claim 1, wherein said composition further comprises a fatty alcohol.

3. The composition of claim 1, wherein said composition further comprises a fatty acid ester selected from the group consisting of a fatty acid ester of butylene and a fatty acid ester of propylene glycol.

4. The composition of claim 3 wherein said oil gelling polymer comprises a $C_2$-$C_4$ alkylcellulose.

5. The composition of claim 1, wherein said UV-absorbing polyester comprises at least one UV-absorbing moiety selected from the group consisting of a UV-A absorbing moiety and a UV-B absorbing moiety.

6. The composition of claim 5, wherein said UV-A absorbing moiety selected from the group consisting of a tertrahydroxybenzophenones, dicarboxydihydroxybenzophenones and alkane ester or acid halide derivatives thereof, dihydroxy-, dicarboxy-, and hydroxycarboxydibenzoylmethanes and alkane ester or acid halide derivatives thereof, dihydroxy-, dicarboxy-, and hydroxycarboxystilbenes and alkane ester or acid halide derivatives thereof, bis(hydroxystyrenyl) benzenes, bis(carboxystyrenyl)benzenes and alkane ester or acid halide derivatives thereof, dihydroxy-, dicarboxy, and hydroxycarboxycarotenes and alkane ester or acid halide derivatives thereof, and 2cyano-3,3-diphenyl acrylic acid, 2-ethyl hexyl ester.

7. The composition of claim 5, wherein said UV-A absorbing moiety is selected from the group consisting of a UV-absorbing triazole and a UV-absorbing dibenzoylmethane.

8. The composition of claim 5, wherein said UV-B absorbing moiety selected from the group consisting of a 4-aminobenzoic acid and alkane esters thereof, anthranilic acid and alkane esters thereof, salicylic acid and alkane esters thereof, hydroxycinnamic acid and alkane esters thereof, dihydroxy-, dicarboxy-, and hydroxycarboxybenzophenones and alkane ester or acid halide derivatives thereof, dihydroxy-, dicarboxy-, and hydroxycarboxychalcones and alkane ester or acid halide derivatives thereof, and dihydroxy-, dicarboxy-, and hydroxycarboxycoumarins and alkane ester or acid halide derivatives thereof.

9. The composition of claim 1, wherein said oil gelling polymer is selected from the group consisting of a $C_2$-$C_4$ alkylcellulose, dibutyl ethylheaxanoyl glutamide and dibutyl lauroyl glutamide.

10. The composition of claim 1, wherein said composition is substantially free of emulsifiers having a molecular weight of about 2000 daltons or less.

11. The composition of claim 10 comprising about 1 percent or less of said non-polymeric UV-absorbers and about 1 percent or less of said emulsifiers having a molecular weight of about 2000 daltons or less.

12. The composition of claim 10 comprising about 0.5 percent or less of said non-polymeric UV-absorbers and about 0.5 percent or less of said emulsifiers having a molecular weight of about 2000 daltons or less.

13. The composition of claim 1 comprising from about 0.5 percent to about 40 percent of said UV-absorbing polyester.

14. The composition of claim 1 wherein said discontinuous oil phase is stable from phase separation from said continuous water phase for about one month or more when maintained at about 20° C. to about 25° C.

15. The composition of claim 1 wherein the molecular weight of said UV-absorbing polyester is about 2000 or more.

16. The composition of claim 1, wherein the composition is prepared by a method comprising:
mixing at least said UV-absorbing polyester with said oil-gelling polymer to form a continuous oil phase;
mixing at least water and a water-gelling polymer to form said continuous water phase; and
mixing said continuous oil phase and said continuous water phase under conditions effective to form said composition comprising said discontinuous oil phase stabilized in said continuous water phase.

17. The composition of claim 1, wherein said composition is substantially free of a UV-screening particle.

* * * * *